United States Patent [19]

Mansuri et al.

[11] Patent Number: 4,610,717

[45] Date of Patent: Sep. 9, 1986

[54] CERTAIN 5-(R-OXY)-1-PHENYL OR (3-(TRIFLUOROMETHYL)PHENYL)-TRIAZOLES, USEFUL FOR CONTROLLING UNDESIRED PLANT GROWTH

[75] Inventors: Muzammil M. Mansuri, Cheshire, Conn.; Alasdair McArthur, Dare, England

[73] Assignee: Shell Oil Company, Houston, Tex.

[21] Appl. No.: 802,795

[22] Filed: Nov. 26, 1985

[51] Int. Cl.[4] ................. A01N 43/647; A01N 43/653; C07D 249/06; C07D 249/12

[52] U.S. Cl. ........................................ 71/92; 546/276; 548/255; 548/262; 548/263; 548/265

[58] Field of Search .................... 71/92; 548/255, 263, 548/265; 546/276

[56] References Cited

FOREIGN PATENT DOCUMENTS 034673 4/1981 Japan .................................. 548/265
049370 5/1981 Japan .
049371 5/1981 Japan .

*Primary Examiner*—Alton D. Rollins

[57] ABSTRACT

Certain 5-(R-oxy)-1-phenyl or (3-(trifluoromethyl)-phenyl)triazoles, useful for controlling undesired plant growth.

8 Claims, No Drawings

CERTAIN 5-(R-OXY)-1-PHENYL OR (3-(TRIFLUOROMETHYL)PHENYL)TRIAZOLES, USEFUL FOR CONTROLLING UNDESIRED PLANT GROWTH

BACKGROUND OF THE INVENTION

Japanese Patent Application No. 56049371 discloses certain N-phenyl-C-aryloxy-1,2,4-triazoles having a very specific substitution pattern on the phenyl ring, and describes their use in controlling plant fungal diseases. There is no teaching therein that such triazoles have any herbicidal activity; in fact the disclosure of plant protectant applications in the Japanese patent leads directly away from the idea of herbicidal activity.

DESCRIPTION OF THE INVENTION

It has now surprisingly been found that certain N-phenyl triazoles do indeed have useful herbicidal properties, and accordingly the present invention provides herbicidal compositions that comprise a carrier and, as active ingredient a N-aryl triazole of the formula:

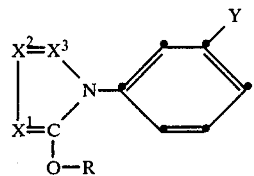

(I)

wherein two of $X^1$, $X^2$ and $X^3$ are nitrogen atoms and the third is $=CR^1—$ wherein $R^1$ is hydrogen or methyl, R is pyridyl, cyclohexyl, phenyl or phenyl substituted by one substitutent selected from halogen, methyl, methoxy, trifluoromethyl and cyano, and Y is hydrogen or trifluoromethyl.

The highest level of activity with respect to plants is shown by those species of the subgenus of Formula I wherein $R^1$ is hydrogen and Y is trifluoromethyl, particularly the individual species wherein R is phenyl, those species wherein R is m-halophenyl, $R^1$ is hydrogen and Y is trifluoromethyl being nearly as active.

It will be appreciated that the alternative meanings for $X^1$, $X^2$ and $X^3$ correspond to the three different isomeric forms of an N-substituted triazole ring; of the three isomeric configurations the 1,2,4 and the 1,2,3 configurations (i.e., wherein $X^2$ or $X^1$, respectively, denotes the $=CR^1—$ group), especially the former, are preferred.

Compounds of Formula I can be prepared by treating a 5-halotriazole of the formula

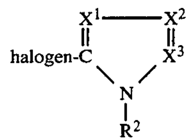

(II)

wherein the halogen atom is bromine or chlorine, and $R^2$ is phenyl or (3-trifluoromethyl)phenyl, with an alcohol or phenol, ROH, or an alkali metal salt of such an alcohol or phenol. This reaction is suitably carried out in an organic solvent, in particular a polar solvent such as dimethylformamide, and preferably in the presence of a base, such as an alkali metal alkoxide, e.g., potassium tert.-butoxide, or potassium carbonate.

The 5-halotriazoles may be prepared by appropriate adaptations of established synthetic methods, which will often differ for the different isomeric forms of the triazole ring. Thus, the 1-$R^2$-5-halo-1,2,4-triazoles may be prepared by reacting a semicarbazide of the formula $H_2N—C(O)—N(R^2)—NH_2$ and the 1-$R^2$-5-halo-1,3,4-triazoles may be prepared by reacting a semicarbazide of the formula $R^1—NHC(O)NHNH_2$, respectively, with an alkyl orthoformate of the formula $R^1—C(O—alkyl)_3$, followed by halogenation, suitably with a phosphorus oxyhalide such as phosphorus oxychloride. An alternative route to the 5-halo-1,2,4-triazoles is by dissolving cyanuric chloride in dimethylformamide followed by reaction with an arylhydrazine of formula $R^2—NHNH_2$ and N-bromosuccinimide.

In the case of the 1,2,3-triazoles of Formula I, a suitable synthetic process is direct cyclization of an azide of formula $R^2—N_3$, which can suitably be effected by reaction with an acetylenic derivative of formula $R—O—C\equiv CH$, or by reaction with a dialkyl malonate, followed by treatment with a phosphorus pentahalide, an alcohol or phenol and R—OH, and removal of the ester group by hydrolysis and heating.

Compounds of Formula I have been found to show interesting activity as herbicides. Accordingly, the invention further provides a herbicidal composition comprising a compound of formula I as defined above in association with at least one carrier, and a method of making such a composition which comprises bringing a compound of Formula I into association with at least one carrier.

The invention also provides the use of such a compound or composition according to the invention as a herbicide. Further, in accordance with the invention there is provided a method of combating undesired plant growth at a locus by treating the locus with a compound or composition according to the invention.

For application, a compound of Formula I ordinarily is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of Formula I.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides—i.e., horticulturally acceptable carriers—are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25 to 75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or (up to 95%) more by weight of finely divided active material, 3–7% by weight of a blend of surfactants, which act as wetting, dispersing, suspending and binding agents, and may contain up to 3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.5% by weight to as much as about 95% by weight of a compound of Formula I as the active ingredient.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula I, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compound of Formula I will be satisfactory.

The following examples described the preparation, isolation and physical properties of typical individual species of the compounds of Formula I, in particular instances. In these examples, the identity of each product, and of any intermediate involved, was confirmed by appropriate chemical and spectral analyses.

EXAMPLE 1

Preparation of 1-Phenyl-3-methyl-5-phenoxy-1,2,4-triazole (1) via semicarbazide route (A) 6.95 g of 2-phenylsemicarbazide was treated with 7.45 g of triethyl orthoacetate in 20 ml of 2-methoxyethanol, under reflux with stirring, and ethanol distilled off. The reaction mixture was concentrated, and the product chromatographically purified to yield, as as solid, m.p. 163°-165° C., the triazolinone (1A) of the structure:

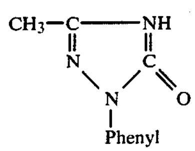

(B) 3.0 g of 1A was heated with 5 ml of phosphoryl chloride in a sealed tube at 200° C. for 2 hours. After cooling, the reaction mixture was poured into ice water, the crude product collected by filtration and purified chromatographically to yield 1-phenyl-3-methyl-5-chloro-1,2,4 triazole (1B), as a solid, m.p.: 81°-84° C.

(C) 0.93 g of potassium tert.-butoxide was added to a stirred solution of 0.71 g of phenol in 15 ml of dry dimethylformamide. When all the butoxide had dissolved, a solution of 1.45 g of 1B in 10 ml of dry dimethylformamide was added and the mixture was stirred and heated at 80° C. for 2 hours. After cooling, the reaction mixture was poured into water and extracted with ether. The ether extracts were washed with 5% aqueous sodium hydroxide, dried and evaporated, and the residue was recrystallized from petroleum ether (40°-60°) to give 1, as a solid, m.p.: 64°-66° C.

EXAMPLE 2

Preparation of 1-(3-trifluoromethylphenyl)-5-phenoxy-1,2,4-triazole (2) via cyanuric chloride route (A) 36.8 g of cyanuric chloride was dissolved in 120 ml of dimethylformamide and the solution was stirred at room temperature. After about 10 minutes an exothermic reaction started and a precipitate formed. The temperature was maintained at 50°-60° C., when the precipitate gradually dissolved and carbon dioxide evolved. When evolution of carbon dioxide had ceased, the mixture was cooled and the crystalline product triturated with acetone, filtered, washed with acetone and dried to give the dimethylammonium salt (2A).

(B) A mixture of 16.4 g of 2A and 17.6 g of 3-trifluoromethylphenylhydrazine were stirred and heated to 60° C. Dimethylamine was evolved in an exothermic reaction and the temperature maintained at 90° C. until evolution ceased (about 30 minutes). After cooling, the reaction mixture was dissolved in ether, washed with water, dried and chromatographically purified to yield 1-(3-trifluoromethylphenyl)-1,2,4-triazole (2B).

(C) 8.52 g of 2B was mixed with 7.83 g of N-bromosuccinimide and ca. 50 mg of benzoyl peroxide in 250 ml of carbon tetrachloride. The resulting mixture was stirred under reflux for 3 hours. After cooling, the reaction mixture was filtered and the filtrate evaporated to yield the bromotriazole (2C) as a brown oil, which was used directly for the next stage.

(D) 1.0 g of potassium tert. butoxide was added to a solution of 0.75 g of phenol in dry dimethylformamide under a nitrogen atmosphere, and when the base had dissolved a solution of 2.3 g of 2C in 10 ml of dry dimethylformamide was added. The reaction mixture was stirred at 70°-80° C. for 2 hours, cooled and poured into ice/water. After standing, the solid product was filtered from the aqueous mixture, washed and dried to yield 2, as a solid, m.p.: 43°-45° C. 2 also was prepared by the procedure of Example 1, using 2-(3-trifluoromethylphenyl)semicarbazide and triethyl orthoformate as starting materials. The product melted at 46°-48° C.

EXAMPLES 3 TO 17

Following procedures analogous to those described in Examples 1 and 2, further 1,2,4-triazole derivatives were prepared, whose physical characteristics are given in Table 1. In the table, the compounds are identified by reference to the substituents in the formula

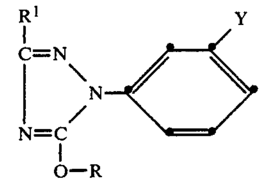

TABLE 1

| Example Number | R | Y | $R^1$ | Melting Point (°C.) |
|---|---|---|---|---|
| 3 | Phenyl | H | H | 48-50 |
| 4 | Phenyl | $CF_3$ | $CH_3$ | 73-75 |
| 5 | 3-F—Phenyl | $CF_3$ | H | 53-54 |
| 6 | 4-F—Phenyl | $CF_3$ | H | 59-60 |
| 7 | 2-F—Phenyl | $CF_3$ | H | 41-43 |
| 8 | 3-Cl—Phenyl | $CF_3$ | H | 70-72 |
| 9 | 3-$CH_3$—Phenyl | $CF_3$ | H | 48-52 |
| 10 | 4-$CH_3$—Phenyl | $CF_3$ | H | 65-67 |
| 11 | Cyclohexyl | $CF_3$ | H | oil |
| 12 | 2-$CH_3$—Phenyl | $CF_3$ | H | 55-58 |
| 13 | 3-$CF_3$—Phenyl | $CF_3$ | H | 58-59 |
| 14 | m-CN—Phenyl | $CF_3$ | H | 105-106 |
| 15 | m-Br—Phenyl | $CF_3$ | H | 70-72 |
| 16 | m-$CH_3O$—Phenyl | $CF_3$ | H | 45-47 |
| 17 | 3-Pyridyl | $CF_3$ | H | 52-53 |

EXAMPLE 18

Preparation of 1-Phenyl-5-phenoxy-1,2,3-triazole (18) from phenoxyacetylene

A mixture of 2.6 g phenylazide and 2.36 g of phenoxyacetylene in 20 ml of benzene was stirred under reflux overnight. The reaction mixture was chromatographically separated to give 18, as a solid, m.p.: 96°-98° C.

EXAMPLE 19

Following a procedure similar to that described in Example 18, but using 3-trifluoromethylphenylazide, 1-(3-trifluoromethylphenyl)-5-phenoxy-1,2,3-trizole (19) was obtained as an oil.

EXAMPLE 20

Preparation of 18 from diethyl malonate and phenyl azide (A) 32 g of diethyl malonate was added to a stirred solution of sodium ethoxide (4.6 g sodium in 80 ml ethanol), 23.8 g of phenylazide was then added dropwise with cooling, after which the mixture was refluxed for 30 minutes. After cooling, the sodium salt of the enol ester formed was filtered off, dissolved in water, washed with ether, and acidified with dilute hydrochloric acid. The resultant yellow oil was recrystallized to yield 1-phenyl-4-ethoxycarbonyl-5-hydroxy-1,2,3,-triazole 20A, as a solid, m.p.: 72°-74° C.

(B) 11.65 g of 20A was mixed with 13.8 g of phosphorus pentachloride, and the mixture was slowly heated to ca. 70° C., when vigorous reaction occurred. When reaction had subsided, heating was continued until evolution of hydrogen chloride ceased (about 1 hour), after which phosphoryl chloride was removed in vacuo, and the residue chromatographically purified to yield 1-phenyl-4-ethoxycarbonyl-5-chloro-1,2,3-triazole (20B), as a solid, m.p.: 80°-81° C.

(C) 2.5 g of potassium tert.-butoxide was added to a stirred solution of 1.9 g of phenol in 45 ml of dry dimethylformamide. A solution of 5.0 g of 20B in 40 ml of dry dimethylformamide was added to the phenoxide solution and the resulting mixture stirred and heated at 80° C. for 2 hours. After cooling, the mixture was poured into water, and the solid product filtered off, washed with water, and chromatographically purified to yield the 5-phenoxy derivative (20C), as a solid, m.p.: 91°-94° C.

(D) 4 g of 20C was hydrolyzed with excess aqueous 1.25M sodium hydroxide, and the product acidified with dilute hydrochloric acid to yield 1-phenyl-4-carboxyl-5-phenoxy-1,2,3 triazole.

(E) 20D was heated until evolution of carbon dioxide ceased, and the product purified chromatographically to yield 18, as a solid, m.p.: 96°-98° C.

EXAMPLE 21-24

Following procedures similar to those described in Examples 18-20, further 1,2,3-triazole derivatives were prepared, whose physical characteristics are given in Table 2. In this Table the compounds are identified by reference to the substituents in the formula

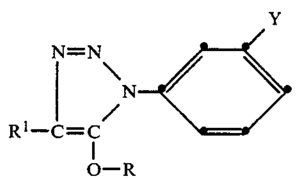

TABLE 2

| Example Number | R | Y | $R^1$ | Melting Point (°C.) |
|---|---|---|---|---|
| 21 | 3-F—Phenyl | $CF_3$ | H | oil |
| 22 | 3-Br—Phenyl | $CF_3$ | H | oil |
| 23 | 4-F—Phenyl | $CF_3$ | H | 63-65 |
| 24 | 2-F—Phenyl | $CF_3$ | H | |

EXAMPLE 25

Preparation of 4-(3-trifluoromethylphenyl)-5-phenoxy-1,2,4-triazole (25)

(A) A solution of 10.95 g of 4-(3-trifluoromethylphenyl)semicarbazide and 7.4 g of triethyl orthoformate in 20 ml of 2-methoxyethanol was stirred under reflux and ethanol continuously removed by distillation. After about 4 hours the reaction mixture was cooled, concentrated in vacuo, and the product recrystallized to yield, as a solid, m.p.: 145°-147° C., the triazolinone (25A) of the structure:

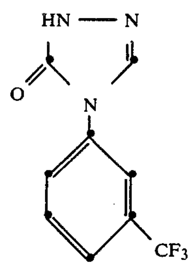

(B) 6.0 g of 25A was heated under reflux with 30 ml of phosphoryl chloride for 45 minutes. The reaction mixture was poured into ice, extracted with chloroform and the extract washed with sodium hydroxide solution and evaporated to yield, as a dark oil, 4-(3-trifluoromethylphenyl)-5-chloro-1,2,4-triazole (25B).

(C) 0.8 g of potassium tert-butoxide was added to a solution of 0.53 g of phenol in 10 ml of dry dimethyl formamide. When all the butoxide had dissolved, a solution of 1.4 g of 25B in 10 ml of dry dimethylformamide (10 ml) was added and the stirred mixture was heated to 75° C. for 90 minutes. The reaction mixture was poured into a large excess of ice-water, the solid product filtered off and recrystallized from hexane/ethyl acetate to give 25, as a solid, m.p.: 83°-85° C.

EXAMPLE 26

Herbicidal Activity

To evaluate their herbicidal activity, compounds according to the invention were tested using as representative range of plants: maize, *Zea mays* (Mz); rice *Oryza sativa* (R); barnyard grass, *Echinochloa crusgalli* (BG); oat, *Avena sativa* (O); linseed, *Linum usitatissisum* (L); mustard, *Sinapsis alba* (M); sugar beet, *Beta vulgaris* (SB) and soya bean, *Glycine max* (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test viz., solid drench and foliar spray tests. In the soild drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trademark TRITON X-155. These acetone solutions were diluted with water and the resulting formulations applied at dosage levels corresponding to 5 kg or 1 kg of active material per hectare in a volume equivalent to 600 liters per hectare in the soil spray and foliar spray test, and at a dosage of level equivalent to 10 kilograms of active material per hectare in a volume equivalent to approximately 3,000 liters per hectare in the soil drench tests.

In the pre-emergence tests untreated sown soil and in the pos-temergence tests untreated soil bearing seedling plants were used as controls.

The herbicidal effects of the test compunds were assessed visually twelve days after spraying the foliage and the soil, and thirteen days after drenching the soil and were recorded on a 0–9 scale. A rating 0 indicates growth as untreated control, a rating 9 indicates death. An increase of 1 unit on the linear scale approximates to a 10% increase in the level of effect.

The results of the tests are set out in Table 3.

TABLE 3

| Compound of Example | Soil Drench 10 kg/ha | | | | | | | | Dosage | Foliar Spray | | | | | | | | Pre-emergence | | | | | | | |
|---|---|---|---|---|---|---|---|---|---|---|---|---|---|---|---|---|---|---|---|---|---|---|---|---|---|
| No. | Mz | R | BG | O | L | M | SB | S | kg/ha | Mz | R | BG | O | L | M | SB | S | Mz | R | BG | O | L | M | SB | S |
| 3 | 3 | 3 | 3 | 0 | 4 | 5 | 3 | 4 | 5 | 5 | 4 | 5 | 6 | 8 | 8 | 6 | 5 | 1 | 0 | 4 | 2 | 2 | 3 | 3 | 0 |
| | | | | | | | | | 1 | 4 | 2 | 3 | 2 | 3 | 5 | 4 | 4 | 0 | 0 | 2 | 1 | 0 | 1 | 2 | 0 |
| 2 | 5 | 5 | 6 | 7 | 6 | 6 | 6 | 4 | 5 | 5 | 4 | 7 | 7 | 7 | 8 | 9 | 8 | 6 | 4 | 9 | 7 | 5 | 8 | 9 | 4 |
| | | | | | | | | | 1 | 3 | 2 | 5 | 5 | 6 | 8 | 8 | 7 | 4 | 2 | 9 | 5 | 1 | 5 | 8 | 0 |
| 1 | 0 | 0 | 0 | 0 | 3 | 3 | 0 | 0 | 5 | 2 | 0 | 3 | 2 | 4 | 5 | 2 | 3 | 0 | 0 | 0 | 0 | 0 | 3 | 0 | 0 |
| | | | | | | | | | 1 | 0 | 0 | 0 | 0 | 3 | 3 | 0 | 3 | 0 | 0 | 0 | 0 | 0 | 0 | 0 | 0 |
| 4 | 0 | 0 | 0 | 0 | 0 | 0 | 0 | 0 | 5 | 0 | 0 | 3 | 0 | 4 | 8 | 7 | 4 | 0 | 0 | 0 | 0 | 0 | 0 | 0 | 0 |
| | | | | | | | | | 1 | 0 | 0 | 1 | 0 | 2 | 3 | 2 | 3 | 0 | 0 | 0 | 0 | 0 | 0 | 0 | 0 |
| 18 | 0 | 0 | 0 | 0 | 0 | 0 | 0 | 0 | 5 | 1 | 0 | 0 | 2 | 6 | 6 | 4 | 4 | 0 | 0 | 2 | 3 | 2 | 6 | 0 | 2 |
| | | | | | | | | | 1 | 0 | 0 | 0 | 0 | 2 | 3 | 2 | 2 | 0 | 0 | 0 | 0 | 0 | 1 | 0 | 0 |
| 19 | 5 | 5 | 6 | 6 | 3 | 3 | 3 | 4 | 5 | 7 | 4 | 8 | 6 | 7 | 7 | 8 | 6 | 6 | 6 | 9 | 7 | 8 | 8 | 9 | 3 |
| | | | | | | | | | 1 | 5 | 3 | 6 | 4 | 6 | 6 | 7 | 6 | 4 | 4 | 9 | 5 | 6 | 4 | 7 | 1 |
| 25 | 0 | 0 | 0 | 0 | 0 | 0 | 0 | 0 | 5 | 3 | 2 | 7 | 3 | 2 | 4 | 6 | 7 | 0 | 0 | 0 | 0 | 0 | 0 | 0 | 0 |
| | | | | | | | | | 1 | 3 | 1 | 4 | 3 | 2 | 2 | 3 | 4 | 0 | 0 | 0 | 0 | 0 | 0 | 0 | 0 |
| 5 | 5 | 4 | 5 | 6 | 4 | 4 | 4 | 2 | 5 | 5 | 5 | 7 | 7 | 8 | 9 | 8 | 5 | 5 | 4 | 9 | 8 | 6 | 9 | 8 | 4 |
| | | | | | | | | | 1 | 3 | 2 | 4 | 5 | 7 | 8 | 5 | 3 | 3 | 2 | 9 | 5 | 5 | 5 | 2 | 1 |
| 8 | 2 | 2 | 5 | 6 | 3 | 2 | 2 | 0 | 5 | 5 | 5 | 7 | 7 | 8 | 9 | 7 | 4 | 3 | 4 | 8 | 6 | 4 | 7 | 6 | 1 |
| | | | | | | | | | 1 | 2 | 3 | 6 | 6 | 8 | 8 | 6 | 4 | 2 | 3 | 7 | 4 | 2 | 2 | 2 | 0 |
| 9 | 1 | 0 | 3 | 4 | 0 | 1 | 1 | 0 | 5 | 4 | 4 | 7 | 7 | 8 | 8 | 8 | 4 | 0 | 3 | 9 | 5 | 2 | 3 | 3 | 1 |
| | | | | | | | | | 1 | 3 | 2 | 4 | 5 | 7 | 8 | 5 | 4 | 0 | 1 | 4 | 3 | 0 | 1 | 0 | 0 |
| 6 | 5 | 3 | 6 | 7 | 5 | 3 | 2 | 2 | 5 | 5 | 4 | 7 | 7 | 8 | 8 | 8 | 4 | 4 | 3 | 9 | 7 | 5 | 6 | 8 | 2 |
| | | | | | | | | | 1 | 2 | 1 | 4 | 5 | 7 | 8 | 5 | 4 | 1 | 1 | 7 | 2 | 2 | 3 | 1 | 0 |
| 7 | 0 | 0 | 0 | 0 | 0 | 0 | 0 | 0 | 5 | 3 | 2 | 4 | 4 | 5 | 5 | 6 | 5 | 3 | 1 | 8 | 6 | 4 | 5 | 5 | 2 |
| | | | | | | | | | 1 | 1 | 0 | 1 | 0 | 3 | 3 | 2 | 2 | 0 | 0 | 3 | 2 | 0 | 0 | 0 | 0 |
| 10 | 0 | 0 | 0 | 0 | 0 | 0 | 0 | 0 | 5 | 2 | 1 | 5 | 5 | 5 | 6 | 3 | 4 | 1 | 0 | 7 | 4 | 0 | 2 | 1 | 0 |
| | | | | | | | | | 1 | 1 | 0 | 1 | 1 | 2 | 4 | 1 | 2 | 0 | 0 | 2 | 1 | 0 | 0 | 0 | 0 |
| 11 | | | | | | | | | 5 | 7 | 4 | 7 | 6 | 7 | 5 | 5 | 6 | 5 | 4 | 8 | 5 | 3 | 4 | 6 | 4 |
| | | | | | | | | | 1 | 5 | 2 | 5 | 4 | 7 | 4 | 4 | 4 | 2 | 2 | 5 | 2 | | | | |
| 13 | | | | | | | | | 5 | 5 | 3 | 8 | 5 | 7 | 7 | 7 | 6 | 4 | 4 | 9 | 7 | 5 | 7 | 5 | |
| | | | | | | | | | 1 | 3 | 2 | 6 | 3 | 6 | 6 | 6 | 6 | 3 | 2 | 8 | 5 | 2 | 6 | 3 | |
| 14 | 5 | 4 | 5 | 5 | 3 | 3 | 4 | | 5 | 6 | | 6 | 3 | 7 | 7 | 4 | 7 | 4 | 3 | 7 | 6 | 6 | 8 | 5 | 2 |
| | | | | | | | | | 1 | 4 | | 4 | 2 | 6 | 7 | | 6 | 2 | 2 | 7 | 4 | 4 | 7 | 5 | |
| 16 | 1 | 2 | 4 | 3 | 8 | 3 | 2 | | 5 | 8 | 5 | 8 | 5 | 7 | 8 | 8 | 8 | 4 | 5 | 7 | 7 | 4 | 6 | 6 | 2 |
| | | | | | | | | | 1 | 5 | 4 | 7 | 3 | 5 | 6 | 7 | 7 | 2 | 4 | | 5 | 2 | 6 | 5 | 1 |
| 17 | 6 | 5 | 6 | 4 | 6 | 6 | 6 | 3 | 5 | 4 | 1 | 5 | 4 | 7 | 6 | 7 | 7 | 2 | 0 | 4 | 4 | 5 | 4 | 7 | |
| | | | | | | | | | 1 | 2 | | 2 | 2 | 5 | 5 | 6 | 6 | | | 4 | 2 | 5 | 4 | 5 | |
| 12 | 0 | 0 | 0 | 0 | 0 | 0 | 0 | 0 | 5 | 7 | 4 | 7 | 4 | 7 | 7 | 7 | 7 | 6 | 6 | 9 | 4 | 4 | 6 | 4 | 0 |
| | | | | | | | | | 1 | 4 | 2 | 4 | 3 | 6 | 6 | 5 | 6 | 1 | 2 | 7 | 2 | 0 | 0 | 3 | 0 |
| 15 | 3 | 5 | 6 | 5 | 3 | 2 | 2 | 1 | 5 | 6 | 5 | 8 | 7 | 6 | 8 | 8 | 7 | 6 | 5 | 9 | 7 | 6 | 7 | 7 | 2 |
| | | | | | | | | | 1 | 4 | 4 | 8 | 5 | 6 | 7 | 7 | 6 | 4 | 5 | 9 | 5 | 5 | 7 | 7 | 2 |
| 21 | 4 | 3 | 4 | 3 | 5 | 3 | 3 | 4 | 5 | 6 | 3 | 8 | 6 | 7 | 7 | 9 | 8 | 4 | 3 | 9 | 7 | 7 | 8 | 9 | 3 |
| | | | | | | | | | 1 | 3 | 1 | 5 | 3 | 6 | 6 | 8 | 8 | 1 | 0 | 7 | 5 | 3 | 6 | 5 | 0 |
| 22 | 0 | 0 | 1 | 1 | 2 | 1 | 1 | 1 | 5 | 4 | 0 | 5 | 5 | 5 | 8 | 6 | 5 | 0 | 0 | 6 | 4 | 3 | 7 | 6 | 0 |
| | | | | | | | | | 1 | 2 | 0 | 2 | 3 | 4 | 7 | 5 | 4 | 0 | 0 | 2 | 0 | 0 | 3 | 6 | 0 |
| 23 | 0 | 0 | 3 | 2 | 2 | 1 | 2 | 0 | 5 | 2 | 1 | 3 | 4 | 5 | 8 | 6 | 5 | 1 | 0 | 4 | 2 | 3 | 6 | 5 | 0 |
| | | | | | | | | | 1 | 0 | 0 | 2 | 2 | 4 | 6 | 6 | 4 | 0 | 0 | 0 | 0 | 0 | 0 | 0 | 0 |
| 24 | 0 | 0 | 0 | 0 | 0 | 0 | 4 | 2 | 5 | 4 | 4 | 5 | 4 | 6 | 6 | 6 | 5 | 0 | 0 | 0 | 0 | 0 | 0 | 0 | 0 |
| | | | | | | | | | 1 | 3 | 2 | 3 | 2 | 5 | 5 | 5 | 3 | 0 | 0 | 0 | 0 | 0 | 0 | 0 | 0 |

We claim:

1. A compound of the formula

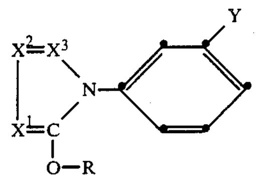

(I)

wherein two of $X^1$, $X^2$ and $X^3$ are nitrogen atoms and the third is $=CR^1-$ wherein $R^1$ is hydrogen or methyl, R is pyridyl, cyclohexyl, phenyl or phenyl substituted by one substituent selected from halogen, methyl, methoxy, trifluoromethyl and cyano, and Y is hydrogen or trifluoromethyl.

2. A compound according to claim 1 wherein $R^1$ is hydrogen and Y is trifluoromethyl.

3. A compound according to claim 1 wherein $X^2$ is $$=\overset{R^1}{\overset{|}{C}}-.$$

4. A compound according to claim 3 wherein $R^1$ is hydrogen and Y is trifluoromethyl.

5. A compound according to claim 2 wherein R is phenyl.

6. A compound according to claim 4 wherein R is phenyl.

7. A method of combatting unwanted plant growth at a locus that comprises applying to the locus an effective amount of a compound according to claim 1.

8. A herbicidal composition comprising an effective amount of a compound of claim 1, together with an inert carrier and a surface-active agent.

* * * * *